United States Patent [19]
Snyder et al.

[11] Patent Number: 5,183,548
[45] Date of Patent: * Feb. 2, 1993

[54] SYSTEM AND METHOD FOR CONTINUOUS SEPARATION OF ISOTOPES

[75] Inventors: Thomas S. Snyder, Oakmont; John F. Jackovitz, Monroeville Boro; Harry M. Ferrari, Fox Chapel, all of Pa.

[73] Assignee: Westinghouse Electric Corp., Pittsburgh, Pa.

[*] Notice: The portion of the term of this patent subsequent to Jun. 18, 2008 has been disclaimed.

[21] Appl. No.: 682,839

[22] Filed: Apr. 9, 1991

Related U.S. Application Data

[63] Continuation of Ser. No. 512,238, Apr. 20, 1990, Pat. No. 5,024,749.

[51] Int. Cl.$^5$ .............................................. B01D 61/42
[52] U.S. Cl. ................................................ 204/299 R
[58] Field of Search ......................... 204/299 R, 180.1

[56] References Cited

U.S. PATENT DOCUMENTS

| | | | |
|---|---|---|---|
| 3,891,413 | 6/1975 | Sievers et al. | 55/4 |
| 3,907,521 | 9/1975 | McConnell | 55/11 |
| 4,584,183 | 4/1986 | Chiang et al. | 423/2 |
| 4,683,042 | 7/1987 | Scott | 204/180.1 |
| 4,711,768 | 12/1987 | Peterson et al. | 423/21.5 |
| 4,767,513 | 8/1988 | Peterson et al. | 204/157.21 |
| 4,900,421 | 2/1990 | Grutzner et al. | 204/299 R |
| 5,024,749 | 6/1991 | Snyder et al. | 204/299 R |

OTHER PUBLICATIONS

"Multicomponent Separations by Continuous Annular Chromotography" Mar. 7, 1989, Industrial Larson Group.

"Pilot-Scale Studies of Sugar Separation by Continuous Chromotography" C. H. Byers.

Primary Examiner—John Niebling
Assistant Examiner—Kathryn Gorgos

[57] ABSTRACT

The invention is both a system and method for continuously separating heavier from lighter isotopes of a particular element, such as zirconium. The system comprises a housing, a column assembly rotatably mounted with respect to the housing which includes a plurality of vertically oriented separation cells arranged in a circle, each of which contains a packing material, both a feed electrolyte source and a barren electrolyte source, each of which has an outlet mounted in the housing for continuously introducing either a feed electrolyte or a barren electrolyte into each of the cells as they rotate past the outlets, and upper and lower electrodes disposed over the upper and lower ends of the separation cells for inducing the electromigration of the lighter zirconium ions toward the lower ends of each of the separation cells. A drain assembly disposed beneath the column assembly continuously collects isotopic enriched electrolyte from the bottom ends of the separation cells. The speed of rotation of the column assembly is coordinated with the rate of eluant flow through the cells so that the same segments of the annular tray of the drain assembly continuously collect eluant enriched in a particular type of zirconium isotope.

14 Claims, 5 Drawing Sheets

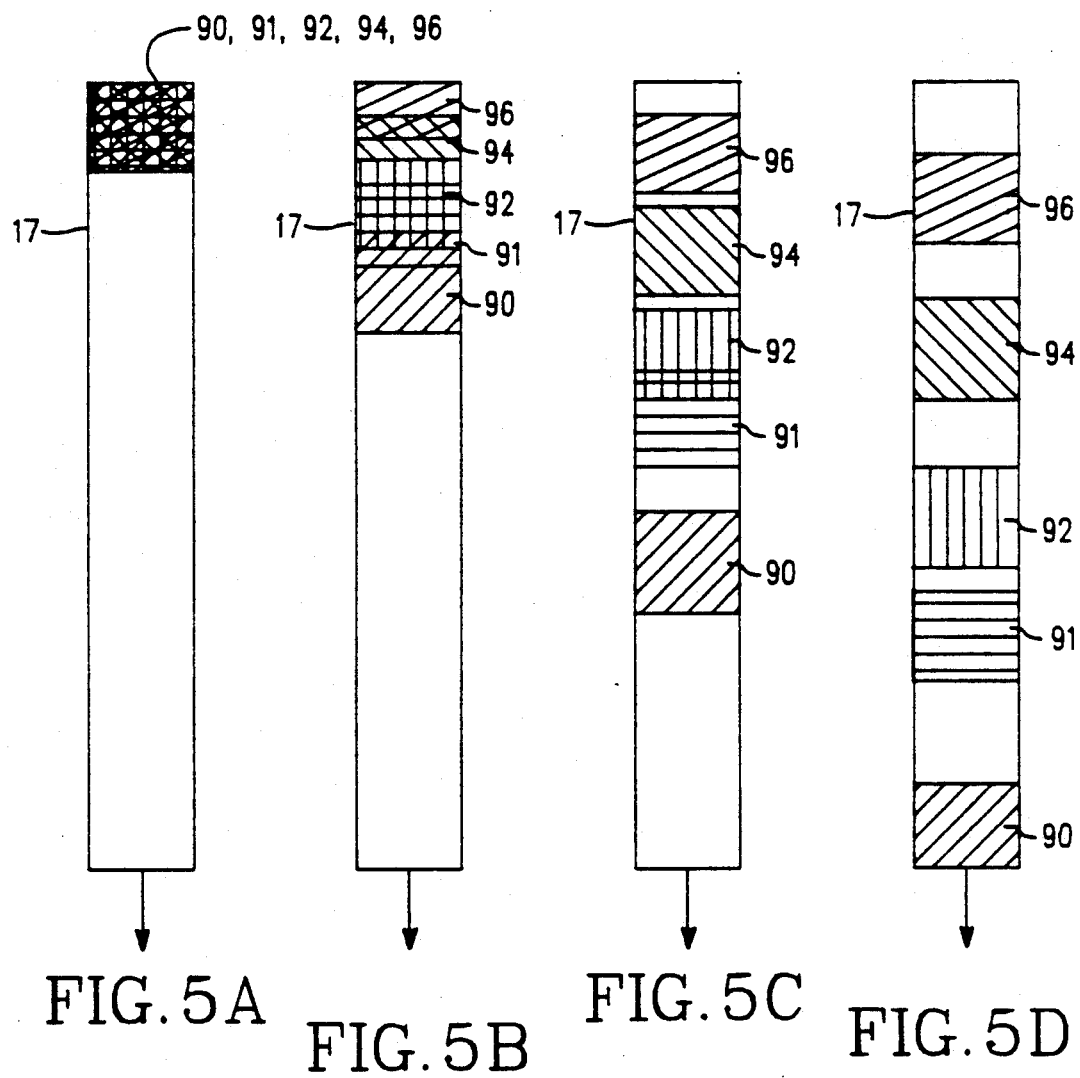

SYSTEM AND METHOD FOR CONTINUOUS SEPARATION OF ISOTOPES

This is a continuation of co-pending application Ser. No. 07/512,238, filed on Apr. 20, 1990, now U.S. Pat. No. 5,024,749.

BACKGROUND OF THE INVENTION

This invention generally relates to isotopic separation, and is specifically concerned with a system and method for continuously separating zirconium isotopes by a combination of balanced ion migration and chromatography.

The use of zirconium for forming fuel rod cladding for nuclear fuels is well known in the prior art. In nature, zirconium exists as a mixture of isotopes which includes zirconium 90, zirconium 91, zirconium 92, zirconium 94 and zirconium 96. Of all these isotopes, zirconium 91 is the least desirable to use in such fuel rod cladding since its relatively high thermal neutron cross-section causes it to absorb thermal neutrons and thereby to impede the uranium fission reaction which is desirable in an operational fuel rod assembly. In naturally occurring zirconium, zirconium 91 constitutes only about 11% of the overall weight of the metal, the balance being constituted by zirconium 90 (51.5%), zirconium 92 (17%), zirconium 94 (17.5%) and zirconium 96 (3.0%). However, because the thermal neutron cross-section of zirconium 91 is 158 times that of zirconium 90, 6 times more than that of zirconium 92, 16 times more than that of zirconium 96 and 18 times that of zirconium 94, the 11% by weight component of zirconium 91 in naturally occurring zirconium counts for 73% of the total thermal neutron cross-section of such zirconium.

The fact that zirconium 91 accounts for almost three quarters of the entire thermal neutron cross-section of naturally occurring zirconium has motivated the development of various isotopic separation techniques designed to get rid of or at least reduce the amount of zirconium 91 in zirconium. In one such technique, a compound of zirconium is vaporized and exposed to a pulse of light generated by a $CO_2$ laser tuned to the vibrations of the bond of either zirconium 90 or 91 and the other constituent atoms joined to the zirconium. The tuned pulses of light cause these bonds to resonate and to break, thus liberating either zirconium 90 or zirconium 91, depending upon the chosen frequency of the light.

While such laser-induced isotopic separation has proven to be effective for its intended purpose, it is unfortunately expensive and capable of separating only relatively small amounts of zirconium isotopes at any given time. Hence it does not lend itself to a scaled-up, bulk-separation process that is capable of inexpensively providing the large quantities of zirconium 91-depleted zirconium needed every year for the fabrication of new fuel assemblies and fuel containers.

Other methods are known which employ electrolytic forces to separate isotopes of other elements, such as potassium. In this technique, ions of naturally occurring potassium are introduced into an electrolyte, which may be an aqueous solution of HCl. The electrolyte and dissolved zirconium ions are introduced into a column filled with an inert particulate material which provides a lengthened tortuous flowpath for the zirconium ions to travel through, and an electric potential is applied across the column. The voltage of this potential attracts potassium ions and hydrogen ions toward the cathode, while simultaneously creating a counter-flow of chlorine ions toward the anode. The voltage is strong enough so that sufficient electrolytic force is applied to the lighter potassium ions to cause a net migration of such ions toward the cathode, but is yet not so strong as to apply such a net migration movement of the heavier ions toward the cathode. Because potassium 41 ions are approximately 5% heavier than potassium 39 ions, they are not as mobile in the liquid medium of the electrolyte, and the electrolytic force applied to them by the cathode is insufficient to overcome the forces of kinetic agitation which causes them to move randomly about the electrolyte in Brownian fashion, and the counter-flow of non-potassium negative ions flowing toward the anode. This combination of forces causes these heavier ions to migrate toward the anode. Because of the balance between the flow of potassium 39 ions toward the cathode and counter-flow of potassium 41 ions toward the anode, no net flow of potassium ions occurs in the electrolyte. Eventually, over a period of time, the region of the electrolyte in the vicinity of the cathode will become enriched in potassium 39, while the region of the electrolyte in the vicinity of the anode will become enriched in potassium 41.

Unfortunately, while the technique of separating isotopes by balanced ion migration has the potential of inexpensively separating bulk amounts of such isotopes, its effectiveness in separating such bulk amounts has thus far been limited by a number of factors. For example, while the weight difference between potassium 41 ions and potassium 39 ions is approximately 5%, the weight differences between zirconium 90 (which constitutes a little over 50% of all naturally occurring zirconium) and zirconium 91 is only about 1%. Hence, the balance that must be struck between the electromigratory forces and the kinetic agitation forces are more difficult to attain and maintain. Additionally, longer migration times through longer column lengths are necessary to achieve the same degree of separation with zirconium isotopes that was achieved with potassium isotopes. Still another limitation associated with the adaptation of prior art potassium isotope separation techniques to zirconium isotope separation stems from the single-column type of device used in the prior art. Such a single column affords batch processing; it does not, by itself, provide the kind of continuous zirconium isotope separation that would be required for practical, large scale production of zirconium that is deficient in zirconium 91. The problem of adapting prior art techniques and methods is further confounded by the fact that, in the case of zirconium, we are attempting to remove the second-lightest of four isotopes, instead of either the lightest or the heaviest of these isotopes from the others. The necessity of removing one of the middle weight isotopes from the others instead of only the lightest or the heaviest isotope again necessitates longer separation times, as well as the maintenance of delicate balances between the electric potential used to create an electromigratory force, and the forces of thermal agitation in the electrolyte.

Clearly, what is needed is a system and method for separating isotopes of an element whose weight differences are only about 1% in a continuous fashion. Ideally such a system and method would be able to effectively remove all or at least most of the zirconium 91 from the balance of zirconium isotopes which occur in naturally occurring zirconium in an economical fashion by means of a system which would be relatively simple and inexpensive to construct and to operate. Such a system and method should be fast in operation, so that large quantities of zirconium which is deficient in zirconium 91 could be produced in short amounts of time. Finally, it would be desirable if the operation of the system and method could not easily be disturbed by either external shock or changes in the ambient temperature.

SUMMARY OF THE INVENTION

Generally speaking, the invention is a system and method for continuously separating a heavier isotope from a lighter isotope of an element that overcomes or at least ameliorates the limitations associated with the prior art. The system of the invention comprises a column assembly including a plurality of vertically oriented separation cells, each of which contains a packing material, a feed electrolyte source having an outlet means that is movable with respect to the upper ends of each of the separation cells for periodically introducing a feed electrolyte into each of the cells that includes ions of the various isotopes of an element, such as zirconium, and a barren electrolyte source having an outlet means that is likewise movable with respect to the upper ends of each of the separation cells for periodically introducing a barren electrolyte into each of the cells. Upper and lower electrodes apply a voltage between the upper and lower ends of each of the vertically oriented cells to induce the electromigration of ions of the zirconium or other element toward the lower electrode and to create a counterflow of other ions, which may be for example chlorine, toward the upper electrode. Finally, the system comprises a drain assembly having a drain that is movable with respect to the lower ends of each of the cells of the column assembly for continuously collecting electrolyte that has been enriched in one of the isotopes of the zirconium or other element through the electromigration process.

In the preferred embodiment, the column assembly is circular, with the vertically oriented separation cells arranged side by side within the confines of a cylindrical housing. The housing is rotatably mounted so that upper ends of each of the vertically oriented separation cells are periodically rotated underneath the outlet of the feed electrolyte source and then beneath one of a plurality of outlets of the barren electrolyte source. The drain of the drain assembly preferably comprises an annular tray that is partitioned off into as many collection segments as the number of vertically oriented separation cells and which further remains fixed relative to the rotating housing that carries the separation cells.

The packing material used in each of the vertical separation cells may be completely inert, but is preferably formed from a material which is capable of enhancing the isotopic separation process through either chromatographic or ion exchange forces. Thus the packing may be formed from sand, an ion exchange resin, or a cation exchange resin.

In the method of the invention, the column assembly commences to rotate relative to both the outlet of the feed electrolyte source and the outlet of the barren electrolyte source. The outlet of the barren electrolyte source saturates each of the separation cells with electrolyte. The outlet of the feed electrolyte source then commences to sequentially introduce a volume of feed electrolyte at the upper ends of each of the vertical separation cells. This feed solution may be, for example, a 0.1–3.0 molar solution of zirconium in the form of zirconium chloride mixed with a 2.0 molar or less solution of HCl. It should be noted that higher HCl concentrations have two effects on zirconium solutions: both the zirconium solubility and zirconium complexation/hydration decrease as HCl concentration increases. Decreasing the zirconium solubility increases the separation vessel size, capital and operating costs. Decreasing the zirconium hydration characteristics improves the separation performance by maximizing mass differences between the isotopes. These two opposing phenomena must be balanced in optimizing the separation.

All during the time period, when the feed solution is introduced, the electrodes located around the upper and lower ends of each of the vertical separation cells have been applying an electrical potential which causes the lighter isotopes of zirconium to flow faster through the column than the heavier isotopes. At the time that ions of the lightest isotope of zirconium begin to flow out through the bottom of the first vertically oriented separation cell, the bottom end of that cell will be disposed over a particular segment of the drain assembly, which will be drained of its isotope-enriched eluent. The speed of the rotational movement of the housing containing the separation cells is coordinated with the times at which the first isotopically enriched eluent begins to flow out of each cell so that the bottom end of each cell is disposed over the same collection segment of the drain assembly when an eluent enriched in a particular isotope of zirconium flows out of the bottom of the cell. Hence, certain selected drain segments of that drain assembly are continuously collecting eluents enriched in a specific zirconium isotope.

BRIEF DESCRIPTION OF THE SEVERAL FIGURES

DETAILED DESCRIPTION OF THE PREFERRED EMBODIMENT

Figure 1:
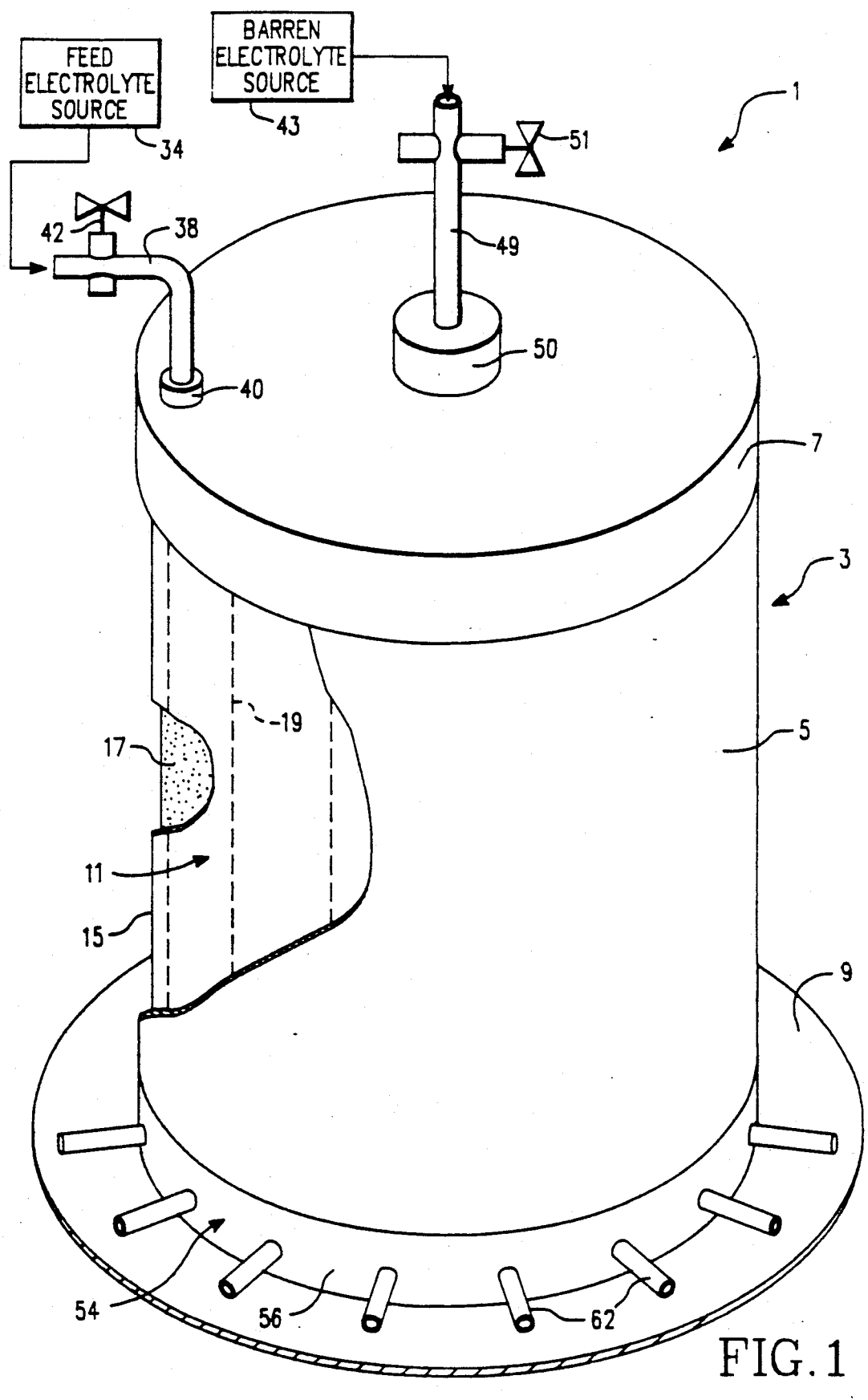
FIG. 1 is a perspective view of the system of the invention, wherein part of the wall of the housing has been broken away to show the column assembly used in the invention.
Figure 2:
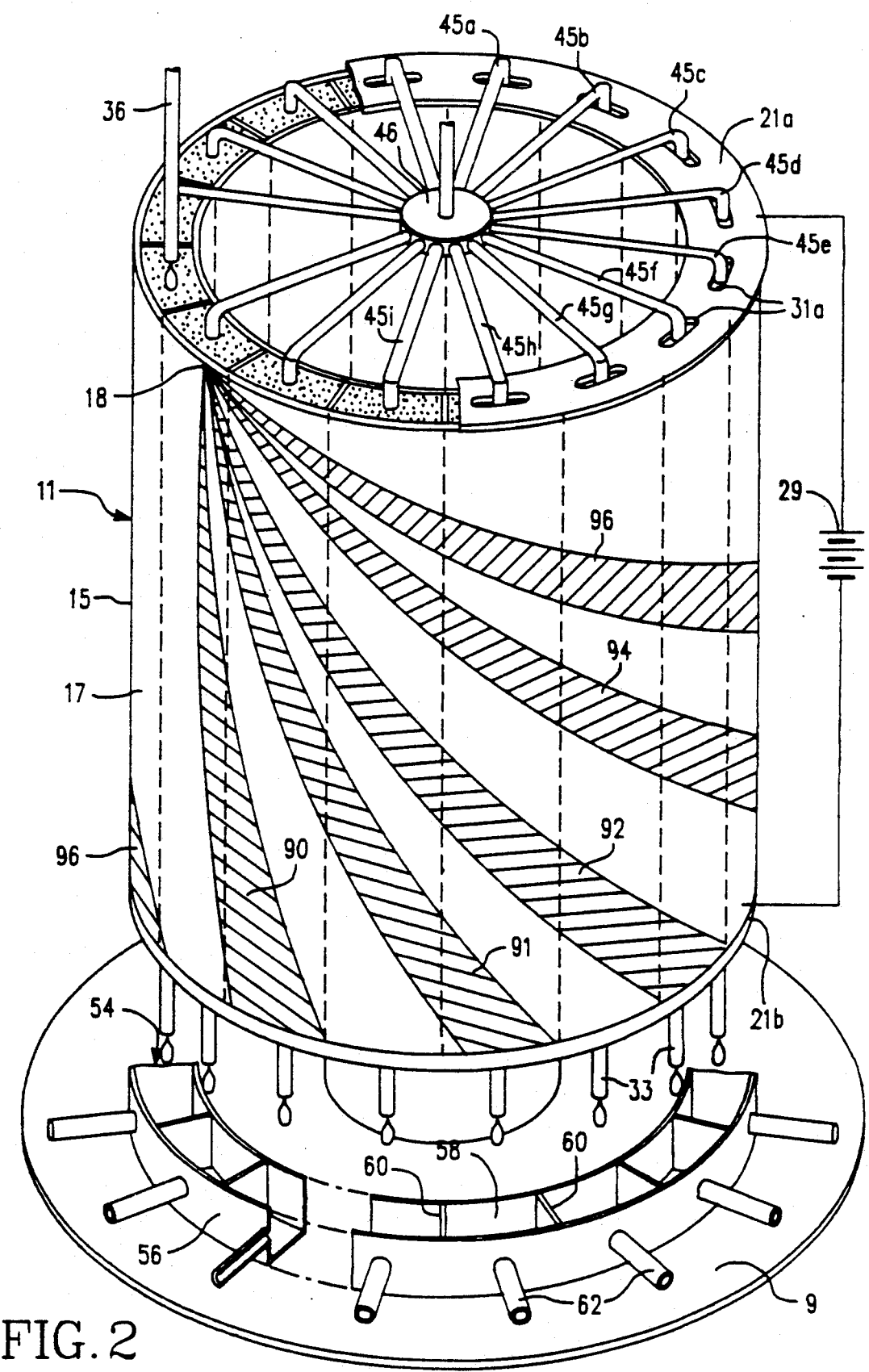
FIG. 2 is a drawing of the separation system illustrated in FIG. 1 with the housing completely removed in order to show the complete structure of the column assembly, the drain assembly and the feed electrolyte and barren electrolyte sources.

With reference now to FIGS. 1 and 2, wherein like numerals designate like components throughout all the several figures, the separation system 1 of the invention generally comprises a housing 3 having a cylindrical wall portion 5, a top cover 7, and a bottom support plate 9. In the preferred embodiment, each one of the housing components 5, 7 and 9 is preferably formed from a non-corrosive metal, which may be stainless steel.

The system 1 includes a column assembly 11 that is contained within the cylindrical wall portion 5 of the housing 3. In the preferred embodiment, column assembly 11 is formed from an inner wall 13 of glass over which an outer wall 15 of glass is concentrically arranged. A plurality of vertically oriented separation cells 17 are defined between the annular space defined between the inner and outer walls 13 and 15 of glass of the column assembly 11. Each of these separation cells 17 is formed from a granular packing 18 confined between a pair of parallel, vertically oriented impermeable partitions 19. Each of the partitions 19 is preferably formed from an inert and impermeable material, such as glass, or any one of a number of inert plastics such as Teflon ®.

The applicants contemplate that the length of each of the separation cells 17 should be about 3 meters or longer, up to about 30 meters. The packing 18 may be simply formed from an inert, granular material such as 100 mesh sand. Such a granular material advantageously impedes the flow of a zirconium-containing electrolyte through the separation cells 17, thereby protracting the time necessary for such an electrolyte to flow through the cell. Additionally, the tortuous path defined by the interstices between the various grains of sand or other inert material forming the packing 18 dampens and otherwise discourages movements in the liquid due to convection currents or other unwanted disturbances, thereby increasing the efficiency of the previously described separation based upon electromigration. However, in the preferred embodiment, the packing material 18 is not inert, but is preferably chromatogaphic in nature and hence capable of chemically adsorbing ionic zirconium as it flows through the separation cells 17 of the column assembly 11. Examples of suitable chromatographic packings include ion exchange resins, in particular a cation exchange resin such as the resin which is popularly sold under the trademark DIAL-X ®. When such a cation exchange resin is used in the packing 18 in lieu of a packing which is simply inert, the zirconium ions will periodically become adsorbed within these resins and then desorbed out of them, and it is believed that the different ionic charge densities associated with the different atomic weights of the various zirconium isotopes will cause the lighter isotopes to adsorb and desorb more rapidly than the heavier isotopes. Such adsorbtion and desorbtion should in turn enhance the effectiveness of the previously described electromigration mechanism in causing the lighter isotopes of zirconium to speed ahead of the heavier isotopes as the electrolyte flows vertically down each of the separation cells 17 due to relative differences in the individual isotopes mass transfer coefficients for transport to and from the beads forming the packing. Ideally, the lighter the element or isotope, the faster its transport. Analytically:

$k$ is proportional to $D^x*[f(m,o,r,v,t \ldots)]$ where $k$ = mass transfer coefficient
$D$ = diffusivity
$m$ = viscosity
$o$ = surface tension
$r$ = density
$v$ = velocity
$t$ = temperature and . . . indicates other variables including geometric influences. Furthermore, D is also proportional to (1/molecular weight)$^y$. Hence $k_{90} > k_{91} > k_{92} > k_{94} > k_{96}$. This is particularly true for systems in which the various isotopes have similar chemical interactions with the packing (i.e., similar retention times). If the heavy isotopes are bound more tightly to the packing (have longer retention times) than the lighter isotopes, separation is further enhanced. If the lighter isotopes interact more strongly, separation is impeded. While a cation exchange resin is preferred, the use of any type of chromatographic packing, such as a reverse phase packing is within the scope of this invention.

Figure 4:
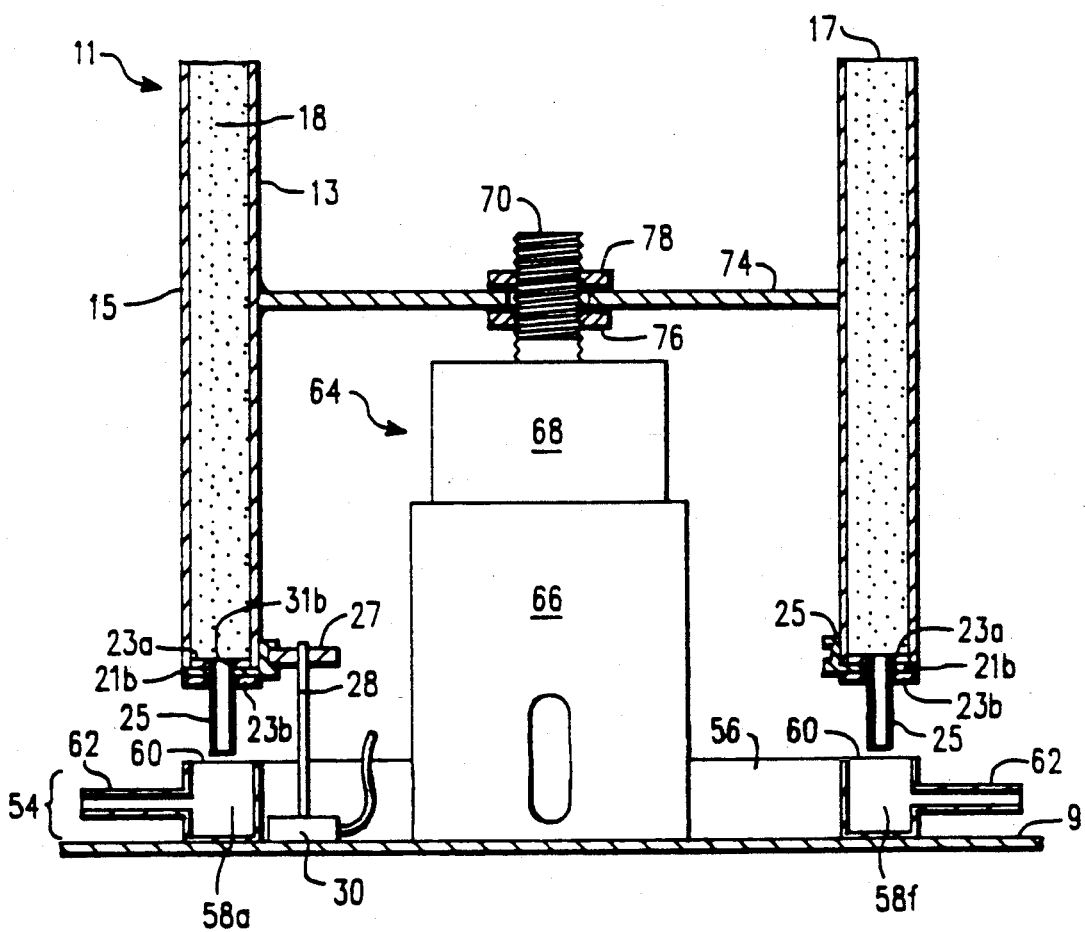
FIG. 4 is a cross-sectional side view of the separation system illustrated in FIG. 2 through the line 4—4, and FIGS. 5A through 5D schematically illustrate how various isotopes of zirconium gradually become separated within a feed electrolyte as it moves from the upper to the lower ends of each of the vertical separation cells of the column assembly.

With specific reference now to FIGS. 2 and 4, both the upper and the lower edges of the column assembly 11 are covered with flat annular electrodes 21a,b. Annular electrode 21a is an anode while annular electrode 21b is a cathode. As best seen with respect to FIG. 4, both sides of each of the flat annular electrodes 21a,b are sandwiched between glass or plastic insulating layers 23a,b. The use of such insulating layers 23a,b obviates the need for constructing the electrodes 21a,b out of an expensive noble metal, such as platinum or gold. Thus, in the preferred embodiment, each of the electrodes 21a,b may be formed from either copper or aluminum. Again with reference to FIG. 4, the inner edges of both the annular electrodes 21a,b are preferably integrally formed into a conductive track 25 into which a contact wheel 27 is received. The contact wheel 27 is in turn rotatably mounted upon a spindle 28 formed from a conductive metal, which in turn is connected to a voltage source 29 by means of a terminal assembly 30. As will be explained more fully hereinafter, the combination of the conductive track 25 and contact wheel 27 allows a constant electrical potential to be applied to be the annular electrodes 21a,b as the column assembly 11 rotates relative to the housing 3 of the system 1. Both of the annular electrodes 23a,b include a plurality of uniformly spaced, fluid conducting openings 31a, 31b, respectively. Each of these openings 31a,b is disposed over one of the cells 17 of the column assembly 11 so that either feed electrolyte or barren electrolyte may be introduced into and out of the cells 17. Each of the openings 31a located in the upper annular electrode 21a is elongated along the circumference of the column assembly 11 to allow electrolyte from either the feed or barren source 34,43 to flow into the cells 17 continuously. Each of the openings 31 located on the lower annular electrode 21b is coupled to a drain nipple 33 which directs the electrolyte or eluent flowing out through the bottom of the cells 17 into the drain assembly 54, which will be discussed in more detail hereinafter.

With reference again to FIGS. 1 and 2, the separation system 1 of the invention includes a feed electrolyte source 34 having a feed outlet 36 which is registrable with the previously described fluid-conducting openings 31 located in the upper annular electrode 21a. This feed outlet 36 is in turn connected to a tubular conduit 38 by way of a coupling 40 mounted on the top cover 7. A flow control valve 42 regulates the rate of flow of feed electrolyte from the source 34 to the outlet 36. A barren electrolyte source 43 is further included within the system 1. This source 43 has a plurality of feed outlets 45a–k which fan out in a spoke-like fashion from a hub-like manifold 47. The circumferential distance between the ends of each of the feed outlets 45a–45k is the same as the circumferential distance between two adjacent separation cells 17. This spacing, in combination with the elongated shape of the fluid conducting openings 31a in the upper annular electrode 21a allows the barren electrolyte source 43 to near continuously introduce barren electrolyte into each of the separation cells 17. As will be discussed in more detail when the operation of the system 1 as a whole is described, the rate of flow of barren flow of electrolyte to each of the feed outlets 45a–45l is equilibrated to the amount of electrolyte that drains out of the bottoms of each of the cells 17, so that a continuous flow of electrolyte occurs through each of the separation cells 17. The hub-like manifold 17 is connected to a conduit 49 by way of a coupling 50 mounted in the top cover 7. A flow control valve 51 controls the rate of flow of barren electrolyte into the manifold 47. In view of the fact that the preferred electrolyte used with respect to zirconium separation is hydrogen chloride HCl, all of the components of both the feed electrolyte source 34 and barren electrolyte source 43 are preferably formed from non-corrosive materials such as glass or appropriate plastics.

With reference now to FIGS. 2 and 4, the system 1 of the invention is further provided with a drain assembly 54 for draining off the electrolyte that flows through the drain nipple 33 of each of the separation cells 17 of the separation column 11. To this end, the drain assembly 54 includes an annular collection tray 56 having segments 58a–58k which are spaced apart the same distance as adjacent separation cells 17 in the column assembly 11. Like other previously described components of the system 1, the entire drain assembly 54 is preferably formed from non-corrosive materials, such as glass or appropriate plastics.

Figure 3:
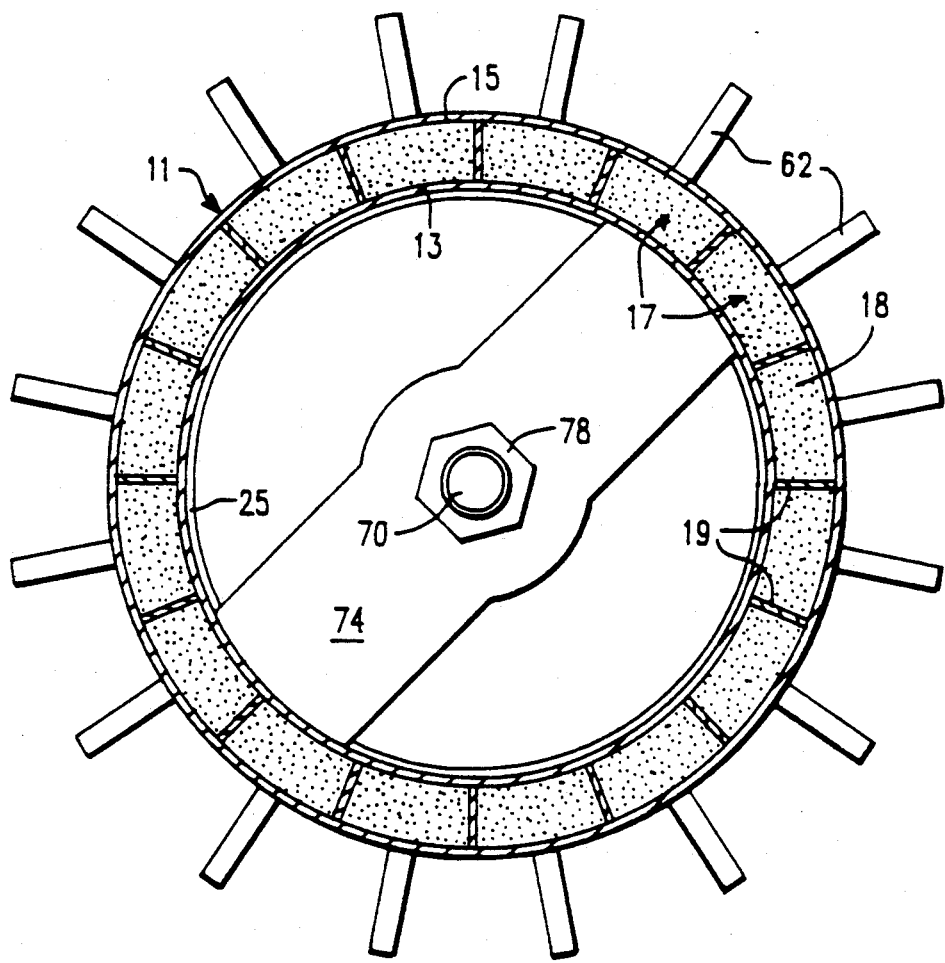
FIG. 3 is a cross-sectional view of the separation system illustrated in FIG. 2 across the line 3—3.

With reference specifically to FIG. 4, the system 1 finally includes a rotary drive assembly 64 for rotating the entire column assembly 11 relative to both the feed electrolyte source 34, the barren electrolyte source 43, and the drain assembly 54. The rotary drive assembly 64 is formed from an electric motor 67 which has been connected to the bottom support plate 9. A drive train 68 mounted over the output of the electric motor 66 reduces the output of the motor 66 to an appropriate value on the order of one revolution per 10 hours. The output shaft 70 of the drive train 68 is receivable through an opening 72 in a mounting bar 74 which, as may best be seen with respect to FIG. 3, traverses and is connected to the inner walls 13 of the column assembly 11. The output shaft 70 is threaded, and is secured to the mounting bar 74 by upper and lower nuts 76, 78.

The method of the invention may best understood with respect to FIG. 2 and FIGS. 5A through 5D. In the first step of the method of the invention, the voltage source 29 is actuated to apply a potential of, for example, five volts between the annular electrode 21a,b. Next, the rotary drive assembly 64 is activated and the barren electrolyte source 43 slowly introduces barren electrolyte into the top ends of each of the separation cells 17 as they rotate past the feed outlet 36 until each cell 17 becomes saturated with barren electrolyte. To this end, the flow valve 51 of the barren electrolyte source is adjusted so that the flow of electrolyte out of the plurality of outlets 45a–45k equals the flow rate of electrolyte through each of the cells 17. In the preferred method, the barren electrolyte is a 2.0 molar solution of HCl, although aqueous HCl solutions having a concentration as high as 6.0 molar HCl may also be used. The rotational speed of the rotary drive assembly 64 is adjusted so that as soon as the first cell becomes completely saturated with barren electrolyte, it is then rotated beneath the outlet 36 of the feed electrolyte source 34. The outlet 36 then introduces a dose of feed electrolyte into the cell 17. In the preferred method of the invention, the feed electrolyte is an aqueous, 2.0 molar solution of HCl and a 0.1–3.0 molar solution of zirconium. Such a zirconium concentration translates into a density of approximately 10–270 grams of zirconium per liter of solution. While any one of a number of water-soluble zirconium compounds may be used to form such a solution, zirconium chloride is preferred due to its relatively high solubility in dilute aqueous HCl solution, and its relatively low expense per unit weight.

As a result of the combined forces of separation applied to the zirconium ions as a result of both electromigration forces and chromatographic forces, the lightest isotope of zirconium, zirconium 90, advances the fastest down through each of the separation cells 17 that have received a dose of feed electrolyte from the feed outlet 36. This is best seen in FIGS. 5A–D. FIGS. 5A represents the distribution of the zirconium ions at the upper end of one of the separation cells 17 immediately after a dose of feed electrolyte has been introduced into its upper end. Over a period of time, the front end of the dose solution becomes progressively more enriched with zirconium 90, while the trailing end becomes enriched with zirconium 96, with the intermediate-weight isotopes of zirconium 91, 92 and 94 fanning out in between the leading and trailing edge of the feed dose. Finally, after a period of time which may be about 10 hours, the zirconium 90 ions reach the bottom of the separation cell 70 and begin to drain out through the drain nipple 33 associated with this particular separation cell 17. The rotation rate that the rotary drive assembly 64 turns the column assembly 11 with respect to the drain assembly 54 is adjusted so that, whenever a particular separation cell 17 begins to drain and eluent which is enriched in zirconium 90, its particular drain nipple 33 will be disposed over the same segment 58 of the annular collection tray 56. While the various segments 58 of the annular tray 56 are portrayed in the various figures as being of equal arcuate length, it should be noted that the tray segments may be advantageously be adjusted so that the drain nipple 33 of a particular cell remains over the same tray segment 58 when an eluent enriched in a particular zirconium isotope is being expelled therefrom.

FIG. 2 illustrates how the system 1 of the invention is capable of producing eluent enriched in anyone of the five different isotopes of zirconium after sufficient time has elapsed, and after the column assembly 1 attains a steady-state. Specifically, when the separation cells illustrated in FIGS. 5A–D are placed immediately adjacent to one another and arranged in a circular form, the eluent stream associated with a specific isotope of zirconium traces a spiral-staircase path around the cylindrical body of the column assembly 11 which is generally helical in shape, wherein the ends of each of the helix is associated with a specific zirconium isotope remain over a specific segment 58 of the annular collection tray 56 of the drain assembly 54. In this manner, an eluent enriched in a specific isotope of zirconium may be continuously harvested.

I claim:

1. An isotopic separation system for continuously separating the isotopes present in a sample containing a mixture of isotopes of a chemical element in ionic form, said system comprising:
   (a) rotatable annulus means having a feed end spaced axially from a discharge end for holding a plurality of circumferentially spaced separation cell means packed with a separation medium for separating said isotopes, wherein each of said separation cell means extends axially from said feed end to said discharge end;

(b) an isotope-containing sample feed source having an outlet means for introducing said sample into each of said separation cell means;

(c) an eluant source having a plurality of outlet means, wherein each said outlet means corresponds to a separation cell means, for introducing eluant into each said separation cell means;

(d) a pair of electrode means for applying an electric potential axially along said annulus means and each of said separation cell means while said annulus means is rotating, thereby causing the separation of lighter isotopes from heavier isotopes in said sample and the enrichment of said eluant with said isotopes; and (e) drain assembly means at the discharge end of said annulus means for continuously collecting eluant enriched with one of said isotopes, including discharge outlet means associated with each said separation cell means for withdrawing isotopically enriched eluant from each said separation cell means.

2. A system as defined in claim 1 wherein each of said separation cell means further includes a drain port located at its discharge end, and said drain assembly means includes an annular collection tray which is uniformly partitioned around its circumference into as many collection segments as there are separation cell means, and wherein the discharge outlet means of said separation cell means are registrable with the segments of said collection tray.

3. A system as defined in claim 1, wherein each said electrode means includes a conductor disposed over the feed and discharge ends of said annulus means.

4. A system as defined in claim 3, wherein each of said conductors is covered by an electrically insulative material, and wherein each conductor includes an opening over each of the feed and discharge separation cell means for conducting eluant through said separation cell means.

5. An isotopic separation system as described in claim 1, wherein said separation medium is selected from the group consisting of cation exchange resins, anion exchange resins, size exclusion media and reverse phase packing.

6. An isotopic separation system as described in claim 1, wherein each said separation cell means is defined by a pair of circumferentially spaced, axially extending impermeable partitions within said annulus means.

7. An isotopic separation system as described in claim 6, further including rotary drive means for rotating said annulus means at a predetermined speed relative to said sample feed source outlet means, said eluant source outlet means and said drain assembly means, wherein said speed is selected to cause isotopically enriched eluant from a selected one of said separation cell means to be discharged at substantially the same location in said drain assembly means.

8. An isotopic separation system for continuously separating the zirconium isotopes present in a sample containing a mixture of isotopes of zirconium in ionic form, said system comprising:

(a) rotatable annulus means having a feed end spaced axially from a discharge end for holding a plurality of circumferentially spaced separation cell means packed with a separation medium for separating said zirconium isotopes, wherein each of said separation cell means extends axially from said feed end to said discharge end;

(b) a zirconium isotope-containing sample feed source having an outlet means for introducing said sample into each of said separation cell means;

(c) an eluant source having a plurality of outlet means, wherein each said outlet means corresponds to a separation cell means, for introducing eluant into each said separation cell means;

(d) a pair of electrode means for applying an electric potential axially along said annulus means and each of said separation cell means while said annulus means is rotating, thereby causing the separation of lighter zirconium isotopes from heavier zirconium isotopes in said sample and the enrichment of said eluant with said zirconium isotopes; and (e) drain assembly means at the discharge end of said annulus means for continuously collecting eluant enriched with one of said zirconium isotopes including discharge outlet means associated with each said separation cell means for withdrawing eluant enriched with one of said zirconium isotopes from each said separation cell means.

9. An isotopic separation system as described in claim 8, wherein said separation medium is selected from the group consisting of cation exchange resins, anion exchange resins, size exclusion media and reverse phase packing.

10. An isotopic separation system as described in claim 8, wherein each said separation cell means is defined by a pair of circumferentially spaced, axially extending impermeable partitions within said annulus means.

11. An isotopic separation system as described in claim 10, further including rotary drive means for rotating said annulus means at a predetermined speed relative to said sample feed source outlet means, said eluant source outlet means and said drain assembly means, wherein said speed is selected to cause eluant enriched with a zirconium isotope from a selected one of said separation cell means to be discharged at substantially the same location in said drain assembly means.

12. A system for separating isotopes of zirconium present in a sample containing at least the isotopes Zirconium-90, Zirconium-91, Zirconium-92, Zirconium-94 and Zirconium 96 in ionic form, said system comprising:

(a) a plurality of axial separation cells spaced circumferentially between an outer wall and a concentric inner wall of a rotatable annulus and defined by impermeable partitions extending between said inner and outer wall, said separation cells being packed from a feed end to a discharge end with a separation medium;

(b) a source of said zirconium isotope-containing sample and a suitable electrolyte, said isotope source including an outlet whereby said sample is continuously introduced into the feed end of said separation cells;

(c) a source of an eluant electrolyte compatible with the suitable electrolyte, said eluant electrolyte source including a plurality of outlets corresponding to said plurality of separation cells whereby said eluant electrolyte is continuously introduced into the feed end of said separation cells;

(d) axial electric potential generating means including a first electrode and a second electrode for applying an electric potential axially between the feed end and the discharge end of the separation cells;

(e) rotary drive means for causing said annulus to rotate simultaneously while said electric potential is being applied; and (f) zirconium isotope collection means including a drain assembly with a plurality of compartments corresponding to said plurality of separation cells for collecting each of said separated isotopes.

13. The zirconium isotope separation system described in claim 12, wherein said separation medium is selected from the group consisting of cation exchange resins, anion exchange resins, size exclusion media and reverse phase packing.

14. The zirconium isotope separation system described in claim 13, wherein said separation medium is a cation exchange resin, the zirconium isotope-containing sample is zirconium chloride, and both the suitable electrolyte and the eluant electrolyte are hydrochloric acid.

* * * * *